(12) United States Patent
Heide et al.

(10) Patent No.: US 11,517,652 B2
(45) Date of Patent: Dec. 6, 2022

(54) MEDICAL DEVICE WITH AN ADDITIVELY APPLIED CONVERTER

(71) Applicant: Fresenius Medical Care Deutschland GmbH, Bad Homburg (DE)

(72) Inventors: Alexander Heide, Eppstein (DE); Dejan Nikolic, Bad Soden (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 565 days.

(21) Appl. No.: 16/495,545

(22) PCT Filed: Mar. 20, 2018

(86) PCT No.: PCT/EP2018/057037
§ 371 (c)(1),
(2) Date: Sep. 19, 2019

(87) PCT Pub. No.: WO2018/172364
PCT Pub. Date: Sep. 27, 2018

(65) Prior Publication Data
US 2020/0093974 A1   Mar. 26, 2020

(30) Foreign Application Priority Data

Mar. 24, 2017   (DE) .......................... 102017106402.8

(51) Int. Cl.
*A61M 1/14*   (2006.01)
*A61M 1/36*   (2006.01)

(52) U.S. Cl.
CPC ............ *A61M 1/14* (2013.01); *A61M 1/3663* (2013.01); *A61M 2205/0233* (2013.01);
(Continued)

(58) Field of Classification Search
CPC .................. A61M 1/14; A61M 1/3663; A61M 2205/0233; A61M 2205/0244; A61M 2205/0294
(Continued)

(56) References Cited

U.S. PATENT DOCUMENTS

| 4,734,184 A | 3/1988 | Burleigh et al. |
| 4,950,244 A | 8/1990 | Fellingham et al. |

(Continued)

FOREIGN PATENT DOCUMENTS

| CN | 101421601 | 4/2009 |
| CN | 105377322 | 3/2016 |

(Continued)

OTHER PUBLICATIONS

International Preliminary Report on Patentability in Application No. PCT/EP2018/057037, dated Sep. 24, 2019, 7 pages (Full English Translation).

(Continued)

*Primary Examiner* — Phillip A Gray
(74) *Attorney, Agent, or Firm* — Fish & Richardson P.C.

(57) ABSTRACT

This disclosure relates to a medical device including a hard part and a converter. The hard part has fluid paths for conducting a medical fluid through the hard part. The converter is arranged to measure a characteristic of the medical fluid while the medical fluid is present in one of the fluid paths. At least a section of the converter is applied or superimposed to the hard part by at least one additive application method.

20 Claims, 4 Drawing Sheets

(52) U.S. Cl.
CPC ............... *A61M 2205/0244* (2013.01); *A61M 2205/0294* (2013.01); *A61M 2205/121* (2013.01); *A61M 2205/3317* (2013.01); *A61M 2205/3331* (2013.01); *A61M 2207/10* (2013.01)

(58) Field of Classification Search
USPC .......................................................... 604/65
See application file for complete search history.

(56) References Cited

U.S. PATENT DOCUMENTS

| | | | |
|---|---|---|---|
| 2003/0042181 | A1 | 3/2003 | Metzner |
| 2009/0012452 | A1 | 1/2009 | Slepicka et al. |
| 2010/0030167 | A1 | 2/2010 | Thirstrup et al. |
| 2011/0011399 | A1 | 1/2011 | Wolpert et al. |
| 2011/0174067 | A1 | 7/2011 | Boiarski |
| 2011/0214504 | A1* | 9/2011 | Bradley ................. G01L 19/14 73/723 |
| 2013/0075314 | A1 | 3/2013 | Nikolic et al. |
| 2016/0067397 | A1 | 3/2016 | Gagel et al. |

FOREIGN PATENT DOCUMENTS

| | | |
|---|---|---|
| CN | 106164636 | 11/2016 |
| DE | 10143137 | 4/2003 |
| DE | 602005006924 | 7/2008 |
| DE | 102009018664 | 10/2010 |
| EP | 1643126 | 4/2006 |
| EP | 2316332 | 5/2011 |
| EP | 2559656 | 2/2013 |
| JP | 2004-512914 | 4/2004 |
| JP | 2010-532217 | 10/2010 |
| JP | 2010-258334 | 11/2010 |
| WO | WO 2002/039086 | 5/2002 |
| WO | WO 2009/009226 | 1/2009 |
| WO | WO 2011/113838 | 9/2011 |
| WO | WO 2015/114635 | 8/2015 |
| WO | WO 2015/200718 | 12/2015 |
| WO | WO 2018/172364 | 9/2018 |

OTHER PUBLICATIONS

International Search Report and Written Opinion in Application No. PCT/EP2018/057037, dated May 22, 2018, 8 pages (Full English Translation).

de.wikipedia.org [online], "'Additive Manufacturing' version difference," Mar. 9, 2017, retrieved on Nov. 16, 2017, retrieved from URL <https://de.wikipedia.org/w/index.php?title=Additive_Fertigung&diff=prev&oldid=163432044>, 10 pages (with English translation).

de.wikipedia.org [online], "'Multi-component injection molding'—version difference," Sep. 17, 2013, retrieved on Nov. 15, 2017, retrieved from URL <https://de.wikipedia.org/w/index.php?title=Mehrkomponenten-Spritzgie%C3%9Fen&dilf=prev&oldid=125364532>, 7 pages (with English translation).

Extended European Search Report in European Appln No. 21208249.9, dated Apr. 4, 2022, 26 pages (with machine translation).

* cited by examiner

MEDICAL DEVICE WITH AN ADDITIVELY APPLIED CONVERTER

CROSS-REFERENCE TO RELATED APPLICATIONS

The present application is the national stage entry of International Patent Application No. PCT/EP2018/057037, filed on Mar. 20, 2018, and claims priority to Application No. DE 10 2017 106 402.8, filed in the Federal Republic of Germany on Mar. 24, 2017, the disclosure of which are expressly incorporated herein in entirety by reference thereto.

TECHNICAL FIELD

The present disclosure relates to a medical device. It further relates to a production method for a medical device, and to a treatment apparatus.

BACKGROUND

Blood treatment apparatuses are connectable to at least one medical device for blood treatment. Such a connectable medical device may be a blood cassette, in which blood is treated or temporarily stored. Some of the connectable medical devices are disposable.

A medical device is thus specified herein, having at least one hard part with complete or incomplete fluid paths for conducting a medical fluid, in particular blood, in the hard part or through the hard part.

The medical device further comprises at least one converter. The converter is arranged to measure a characteristic of the medical fluid or of another fluid while the fluid is present in the fluid path. Alternatively or additionally, the converter is arranged to measure a characteristic of the medical device or to measure an effect, for example, of external or internal pressure applied to the medical device.

The converter is at least in a section thereof applied and/or generated or established directly or indirectly on the hard part by exactly one or by at least one additive application method, preferably a printing method.

The method described herein, serves the production of a medical device. It encompasses providing a hard part of the medical device which comprises fluid paths, a fluid system or sections thereof for a medical fluid.

Further, the method encompasses the application of at least one converter on (at least in a section thereof) the hard part by at least one additive application method, preferably a printing method.

The treatment apparatus described herein comprises at least one multipole connector for the connection with the multipole connecting device (this term may be interchanged also with "multiple connecting device" within the scope) of a medical device.

The treatment apparatus described herein may be configured to receive and process the signals received by the multipole connector.

The treatment apparatus described herein may be connected to a medical device.

In all of the embodiments herein, the use of the expression "may be" and "may have" etc. is synonymous to "is preferably" or "has preferably," etc. respectively, and is intended to illustrate an embodiment.

Embodiments may comprise one or several of the aforementioned or following features. In this way, the features mentioned herein may in any combination thereof be subject-matter of the embodiments unless the person skilled in the art recognizes a concrete combination as technically impossible. Furthermore, embodiments are subject-matter of the dependent claims.

Whenever numerical words are mentioned herein, the person skilled in the art will recognize or understand them as indications of numerical lower limits. Unless it leads the person skilled in the art to an evident contradiction, the person skilled in the art will comprehend the specification for example of "one" encompassing "at least one". This understanding is also equally encompassed as the interpretation that a numeric word, for example, "one" may alternatively mean "exactly one", wherever this is evidently technically possible for the person skilled in the art. Both are encompassed and apply herein to all used numerical words.

The information "top" and "bottom" are to be understood, in case of doubt by the person skilled in the art, as absolute or relative spatial information which refer to the position of the respective component during its intended use.

In some exemplary embodiments described herein, the hard part (being herein also denoted as hard body or as substrate), and/or its accessories like tubes, etc., are to be understood as the part which is usually produced by an injection molding process and therefore referred to herein as "hard" body of the medical device, wherein the hard body may be covered by a comparatively "soft" film. The hard part may be made of PP (polypropylene), PE (polyethylene), PA, ABS, PMMA, PC, PVC or of other polymer sufficiently known to the person skilled in the art or of other materials. It may be made of insulator materials, such as in particular, e.g., ceramic.

In several exemplary embodiments described herein, the hard part (being herein also denoted as hard body or as substrate) is to be understood as being only the part of the medical device which is usually made in an injection molding process, hence denoted as "hard" body, and not the attachments thereof like tubes etc., wherein the hard part may be covered by a comparatively soft film.

The terms sensor and sensor arrangement are used, within the scope of the present description, synonymously for a system comprising or consisting of a converter, signal transmission components and/or evaluation unit. The converter is thereby to be understood preferably as a section of the sensor provided on the device side which is—preferably directly or indirectly—in contact and/or in measure relation with the measuring medium. The converter converts the result of its measurement into suitable signals, e.g. current or voltage signals. The signal transmission components likewise belonging to the sensor arrangement forward the result of their measurement to the evaluation unit, which in the prior art is usually provided on the machine side.

In some exemplary embodiments described herein, the application method encompasses or consists of applying conductive ink.

Conductive ink is understood here to mean fluids with, e.g., nanoparticles or microparticles which if appropriately tightly applied together form a functional path such as, e.g., a conductive path (also referred to herein as an electrode) through which, e.g., signals may be transmitted. In the context of the present disclosure, other materials than conductive ink may as well be considered. Ideally, conductive ink may be biocompatible, but does not have to. Additionally or alternatively, living cells, proteins, etc. may be part of the ink—possibly also—rendering it conductive.

The conductive ink or the alternative material may be used in any aggregate conditions. In some embodiments, an aggregate condition may be understood within the context of the present disclosure to mean a solid or liquid hydrogel in which a biomarker is incorporated. Frozen (i.e. solid) substances or microencapsulated active ingredients/reagents may also be processed. Paths may also be separated from the gas phase by sublimation/condensation.

Conductive ink is here also to be understood as e.g. liquids which comprise carbon-conducting polymers, metal particles and/or combinations thereof, moreover as metalized ink.

An aerosoljet printing technique is considered to be an example for an additive application and, in particular, for printing. The technique disclosed therein and the device described therein for carrying out this technique are suitable for this purpose, in particular also because of the geometric design of the nozzle tip, which allows the necessary number of degrees of freedom for the movements during the printing process.

The present invention is of course not limited to the use of the aerosoljet. The person skilled in the art recognizes that all additive and/or template-free printing methods, in particular by which conductive ink may be applied in the sense of this description, are encompassed by the present disclosure.

In some exemplary embodiments described herein, an application method encompasses an application in several layers.

In some exemplary embodiments described herein, an application method encompasses a sequence or succession of independent application methods or steps belonging to one and the same application method.

In some exemplary embodiments described herein, the additive application encompasses and/or consists of so-called additive manufacturing or generative production methods.

In particular, the following methods are to be understood herein:
Selective Laser Melting (SLM),
Selective Laser Sintering (SLS),
Selective Heat Sintering (SHS),
Binder Jetting (solidification of powder material by binder)
Electron Beam Melting (EBM)
Fused Deposition Modeling (FDM or Fused Filament Fabrication (FFF)),
application welding or cladding,
Wax Deposition Modeling (WDM),
Contour Crafting,
Metal Powder Application methods (MPA),
Cold Gas Injection
Stereolithography (SLA)+micro-SLA,
Methods using Digital Light Processing (DLP) for exposure to light
Liquid Composite Molding (LCM).
Laminated Object Modeling (LOM),
3D screen printing of metals and
Light-controlled electrophoretic deposition.

In some exemplary embodiments described herein, the application method encompasses, or is, a template-free application.

In some exemplary embodiments described herein, a template-free application is to be understood as application without using a template or mask.

In some exemplary embodiments described herein, the application method is no template ink printing, no ink stencil printing, no screen printing, no photo-lithographic process, in particular not in a respective continuous method.

In several exemplary embodiments described herein, the application method is, or encompasses, no gluing or gluing method, no welding and/or no brazing.

In some exemplary embodiments described herein, a template-free application is to be understood as waiver of any auxiliary layer or bezel which needs to be removed subsequently.

Applying using a template may be understood herein as shadowing or protecting shading, in a suitable form, of areas which must not be coated. Such applying takes place, for example, by bezel (e.g. screen printing, spray lacquering etc.) or by lacquer templates (e.g. wafers, printed circuit boards, etc.).

In some exemplary embodiments described herein, the medical device comprises a plurality of converters, for example, two or more, each of which, at least in one section thereof, is directly or indirectly applied to the hard part by an additive application method, preferably a printing method.

In some exemplary embodiments described herein, further sections of a sensor arrangement or of multiple sensor arrangements have been additively applied, preferably using the same application method.

In some exemplary embodiments described herein, the sections of the one sensor arrangements or of the multiple sensor arrangements applied by an additive application method have been applied in the same production step.

In some exemplary embodiments described herein, the sections applied by an additive application method comprise in addition to the at least one converter at least conductors, electrodes, a multipole connecting device or respectively several thereof.

In some exemplary embodiments described herein, the converter(s) is/are arranged or configured for measuring or determining the conductivity, concentration, pressure, voltage or current.

In some exemplary embodiments described herein, the application method results in a 2-dimensional or a 3-dimensional application and/or the converters and/or the further sections applied by an additive application method have been applied by the application method 2- or 3-dimensionally.

In some exemplary embodiments described herein, at least one multipole connecting device has also been applied with the first application method or concurrent to the first application method.

In some exemplary embodiments described herein, a second application method, optionally similar to the first one, was used to apply the sections applied by additive application methods.

In some exemplary embodiments described herein, sections of the converter(s) or of the further section of the at least one sensor arrangement have been applied by a spraying method, e.g. as two-component printing, e.g. by conductive polymers.

In several exemplary embodiments described herein, the converter is no or encompasses no LED (light emitting diode) or OLED (organic light emitting diode) and/or no photo detector.

In some exemplary embodiments described herein, the medical device is a blood cassette. It may be provided for a single use in the blood treatment.

In some exemplary embodiments described herein, the method further encompasses at least one of the following steps: post-processing steps, in particular on the conductive paths or electrodes, as e.g. grinding, polishing, insulating, application of further functional layers of other material;

additive application, e.g. by printing, of the signal connection to the machine interface; additive application, e.g. by printing, of the multi connecting device.

Both the conductive path (also referred to herein as signal conductor) and the multi-connecting device may be applied planarly (i.e. 2-dimensionally) or 3-dimensionally with one or several additive and template-free printing techniques. Here, too, one or more post-processing steps, as described above for the conductive path, are optionally encompassed.

In some exemplary embodiments described herein, the method further encompasses combining two or more sections or components of the medical device which were processed by additive application as described herein.

In some exemplary embodiments described herein, the medical device is a tube, tube system, a tubing set, a blood cassette or a respective part thereof.

A "medical fluid" in the sense of the present disclosure includes each medical liquid and/or each medical gas as well as any combinations. The fluid is preferably blood.

A medical device according to the present disclosure may be a disposable component or a disposable article, which is e.g. made of plastic material.

The medical device according e present disclosure may be produced by an injection molding process.

The medical device according to the present disclosure may have liquid and/or gas connections, half-open channels and/or chambers. One or more cover elements, such as membranes or foils, may serve to close and/or seal the channels and chambers.

The blood treatment, for which the medical device is used, may, for example, be a dialysis method, a hemodialysis, hemofiltration, hemodiafiltration and the like.

In certain exemplary embodiments described herein, the medical device is a blood cassette. The hard part in such examples is a cassette body or cassette main body or a tube section.

In certain exemplary embodiments described herein, the medical device further comprises at least two connectors for pump tube segments for peristaltic pumps, with or without the pump tube segments.

In certain exemplary embodiments described herein, the medical device has a single-needle sterile membrane.

In certain exemplary embodiments described herein, the apparatus comprises strain gauges (DMS sensors). The deformation of the ground results in a change in the length of the measuring path and changes its resistance. Alternatively, a material with piezoelectric properties could also be printed, e.g. PVDF (polymer) or piezoceramic. With the aid of the piezoeffect, preferably (fast) pressure changes or vibrations would be measured.

In certain exemplary embodiments described herein, the treatment apparatus is a blood treatment apparatus, in particular an apheresis apparatus or dialysis apparatus, in particular a hemofiltration apparatus, a hemodiafiltration apparatus, a filtration apparatus or an apparatus for extracorporeal gas exchange.

In certain exemplary embodiments described herein, the treatment apparatus comprises actuators such as e.g. pumps or valves and/or mechanical or non-mechanical interfaces for acting on the medical device through these actuators.

In certain exemplary embodiments described herein, the treatment apparatus does not comprise the converter which is arranged on the medical device. If the medical device comprises, for example, a pressure sensor as a converter, then no machine-side pressure sensor is incorporated into the signal communication between converter and output of a signal measured by the latter, in particular no pressure sensor which would mechanically act on the medical device.

In certain exemplary embodiments described herein, the multipole connector of the treatment apparatus comprises a voltage line, by which the medical device is supplied with electrical voltage. The electrical supply may be used for the data read-out as well as for operating the sensors of the medical device.

Examples of converters in the sense of the present disclosure include:
1) Converters for capacitive measurements: A dielectric is placed between two conductive surfaces. The property to be measured has an interaction with the dielectric constant of the dielectric and may be determined by the condenser properties. With this type of converters, the following, amongst others, may be determined: Conductivity, level (filling level or presence of a liquid), pressure, distance (proximity sensor).
2) Converters for resistance measurement: External effects on a wire influences its resistance. With this type of converter, the following, amongst others, may be determined: Temperature, pressure (strain gauges DMS), weight, force, path, contact (yes, no).
3) Converters based on the piezoeffect: A piezodot (e.g. PVDF) is printed on the surface of a measuring cell. Measuring principle based on pressure reception, for example, directly converting the exterior pressure into tension or based on generating ultrasonic (spatial measuring (running time) or density measurements (amplitude) with a second piezodot as receiver in transmission or based on reflection with only one piezodot. With this type of converter, the following, amongst others, may be determined: Air detection, flow measurements, blood detection, spatial measurements (see underwater microphones, screws with applied piezo pressure sensors for tension force monitoring).
4) Magneto-inductive converter: Known disposable MID sensor for measuring flow or conductivity—in this variant, the electrodes are not inserted in the disposable and coated, but printed instead.
5) Optical converters: A reagent is printed onto the measuring surface. It is irradiated either externally or by a likewise printed optical emitter (diode). The properties of the reagent in terms of reflection, absorption, luminescence, fluorescence depend on the parameter to be measured. The information may be obtained by a photodetector, which detects the corresponding intensity. In this, the photodetector may preferably be mounted on the machine side; the converted signal is transmitted via optical conductors to the multi-connecting device and from there to the machine side. With this type of converter, the following, amongst others, may be determined: Discoloration by temperature, pressure, chemical change, pH, pO2, glucose concentration (Hydrogel Optrode).

Some or all of the embodiments of the present disclosure may have one or more of the advantages mentioned above or in the following.

Modern medical systems for blood treatment usually comprise a blood treatment apparatus (on the so-called "machine side") and medical devices (on the so-called "device side") attachable thereto. If the medical device is a disposable, the so-called "disposable side" is also referred to herein. Although the present invention is not limited to disposables, reference is exemplarily made also to disposable medical devices, without being limited thereto. The disposables used for a blood treatment session are discarded for reasons of hygiene after the blood treatment session because they came into, or might have come into, contact with the patients' blood.

In order to monitor the treatment, sensors and actuators, which measure parameters on the disposable article or on the medical device or which act on the latter, are required.

A functionalization of the disposable itself, for example, the integration of all the respective sensors necessary for monitoring a specific parameter in the disposable, has so far been found to be economically unprofitable because the comparatively expensive sensor components would be discarded after each use. Therefore, conventional disposables for medical blood treatment are usually very simple, essentially consisting of the tube for passage or flow of blood. For the above-mentioned reason, they usually do not carry sensors.

These sensors and actuators are consequently provided in the state of the art largely on the machine side. From there, they effect, or are in interaction with, the medical device via a plurality of sensor and/or actuator interfaces. These interfaces generally determine the form factor or design and lead to the fact that medical systems of the prior art cannot be embodied as small as desired.

Some devices provide a cost-effective disposable. The device can miniaturize the blood treatment systems used and reduce both the extracorporeal blood volume and the effort required for extracorporeal conveyance and hydraulics. The device also provides effective positioning of sensor components on the medical device, and provides a method in which all sensor components arranged on the device side may be integrated in the same production process, which may further reduce the production efforts.

A complete functionalization or only a partial functionalization of the device may reduce the cost per disposable as the device can be discarded together with the converter without significant economic loss due to the particular manner with which the converters are positioned on the device.

For example, with respect to a converter, a partial functionalization is understood to mean that the core task of the converter, for example, detecting a physical, chemical or other parameter or value as well as converting this parameter into an electromagnetically transferrable substitute value, takes place on the medical device itself, either invasively (for example, in contact with blood or a treatment liquid) or non-invasively. However, e.g. the processing of the signals and the interpretation as well as further steps, requiring more sophisticated, e.g. integrated electrical components, is carried out on the machine side. However, in some cases, some or all of the signal processing may also be carried out completely on the machine side. In the latter embodiment, a complete functionalization is mentioned: at least one sensor arrangement or one sensor, is completely additively applied to the device. In this, the device-side components of a sensor arrangement or of a sensor may be applied using the same template-free and additive production method as described supra.

It is also advantageous that, as proposed too, disposables, disclosed herein, when equipped with individual complete sensors, may thus be fully functionalized. The herein-presented method for applying converters or other components of sensors makes this possible.

The partial functionalization and, hence, the remain of the complex electronics necessary for the post-processing and evaluation of the signals on the machine side is therefore advantageous in that the often simpler-designed components of the respective sensors which are applied by the same additive and template-free printing technology are arranged on the device.

Furthermore, the functionalization is economically advantageous, since the production can be made extremely cost-effective by the common use of the same production technology, ideally in the same production step for all sensor components arranged on the device side.

Since the production method disclosed herein is preferably an additive, template-free printing method, a modified version of the device, e.g. with new sensor geometries, may optionally even be produced by just simply loading or installing the corresponding data record in the software. There is no need to make changes in the production hardware, such as, e.g. the purchase of an injection mold, which would be necessary in the production of the medical device by injection molding. This aspect, too, simplifies the manufacturing and improves the cost-effectiveness.

A further advantage of the devices and methods disclosed herein with regard to conventional (non-functionalized) systems is that the physical or chemical parameter to be measured does not need to be guided mechanically to the machine side, as it is the case, e.g., with known pressure sensors within which the pressure conditions to be measured are guided via a pneumatic line to a measuring membrane which is not disposable and is arranged on the machine side. In order to protect the membrane from liquid, complex protective membranes are required regularly, which are referred to as transducer protector (TP). All mechanical interfaces to the machine may thus be omitted. All parameters to be measured may be converted at least into analogue electromagnetic signals (current, voltage, optical signals) by the integrated parts of the sensor system, and may be transmitted only in this form to the processing and evaluation unit on the machine side. For coupling the entire device-side sensor system, only one corresponding multi-channel electromagnetic and/or optical interface is required (multi-connecting device), which allows a significant reduction of the latter.

A further advantage is the multi-connecting device or multipole connecting device of the treatment apparatus. This may also contribute to the fact that there is no need for complete sensors to be present in the treatment device, which for the measuring of the respective parameter mechanically act on the medical device, e.g., a disposable cassette. As a result, the dimensions can be greatly reduced, and the machine side becomes a docking station, which means that by choosing the type of the medical device and, possibly, the selection of the corresponding control program in the control unit of the treatment device the therapy and the related therapy method is determined.

Furthermore, sources for machine/patient contamination are eliminated: pressure measurement in the machine which, in the prior art, must be secured, e.g., by a sterile membrane.

In the following, the present invention is described with reference to the accompanying drawings. In the drawings, identical reference numerals denote similar or identical elements. The following applies:

DETAILED DESCRIPTION OF THE FIGURES

Figure 1:
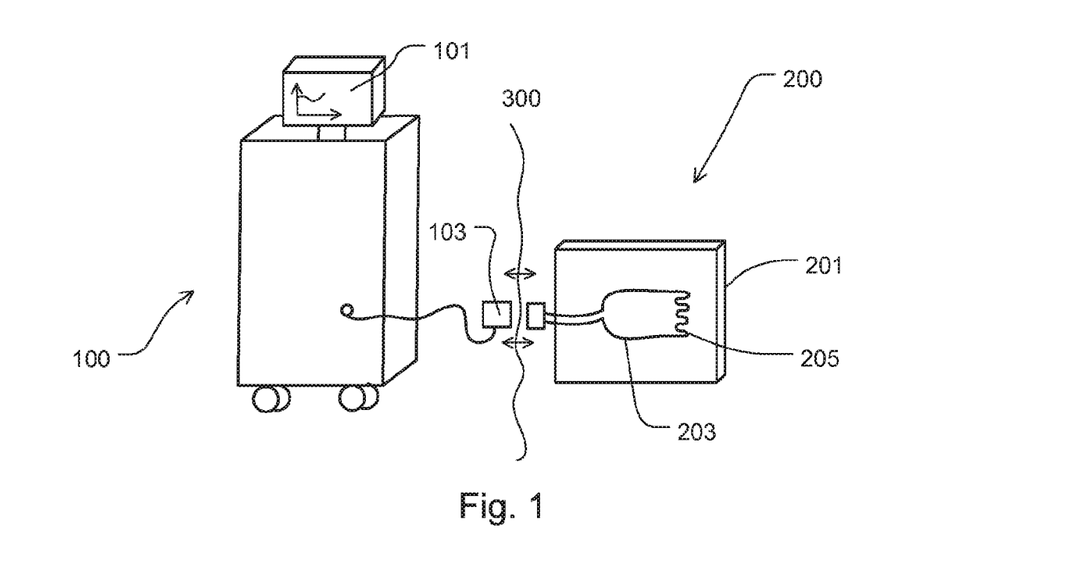
FIG. 1 shows a medical system for blood treatment with a medical device as a partially functionalized disposable.

FIG. 1 shows a very schematic and only exemplarily blood treatment apparatus 100 with a medical device 200 (in short: device 200).

The device 200 is exemplarily designed as a disposable. It was partially functionalized by an additive, template-free printing method.

The blood treatment apparatus 100 and the device 200 are connected to each other in signal communication via an interface 300.

The device 200 comprises a hard part 201. Parts of a sensor arrangement, here a conductor 203 and a converter 205, are provided on the hard part 201.

The converter 205 may be, for example, a pressure sensor. The converter 205 can be printed on the hard part 201. On the disposable side, the converter 205 can only convert the parameter to be measured, here pressure, into an analogue electrical signal.

Via the additively printed conductor 203, the electric signal is conducted to the defined interface 300 which is connected to a machine-side evaluation unit indicated by a monitor 101 for displaying the results obtained by the evaluation unit.

On the machine side, the signal can be digitized by an AD (analog-to-digital) converter or AD converter 103. Post-processing steps (filtering, smoothing, Fourier transformation, zero filling etc.) may take place prior to a final evaluation and interpretation. All these optional steps can be performed, e.g., in the evaluation unit.

Figure 2:
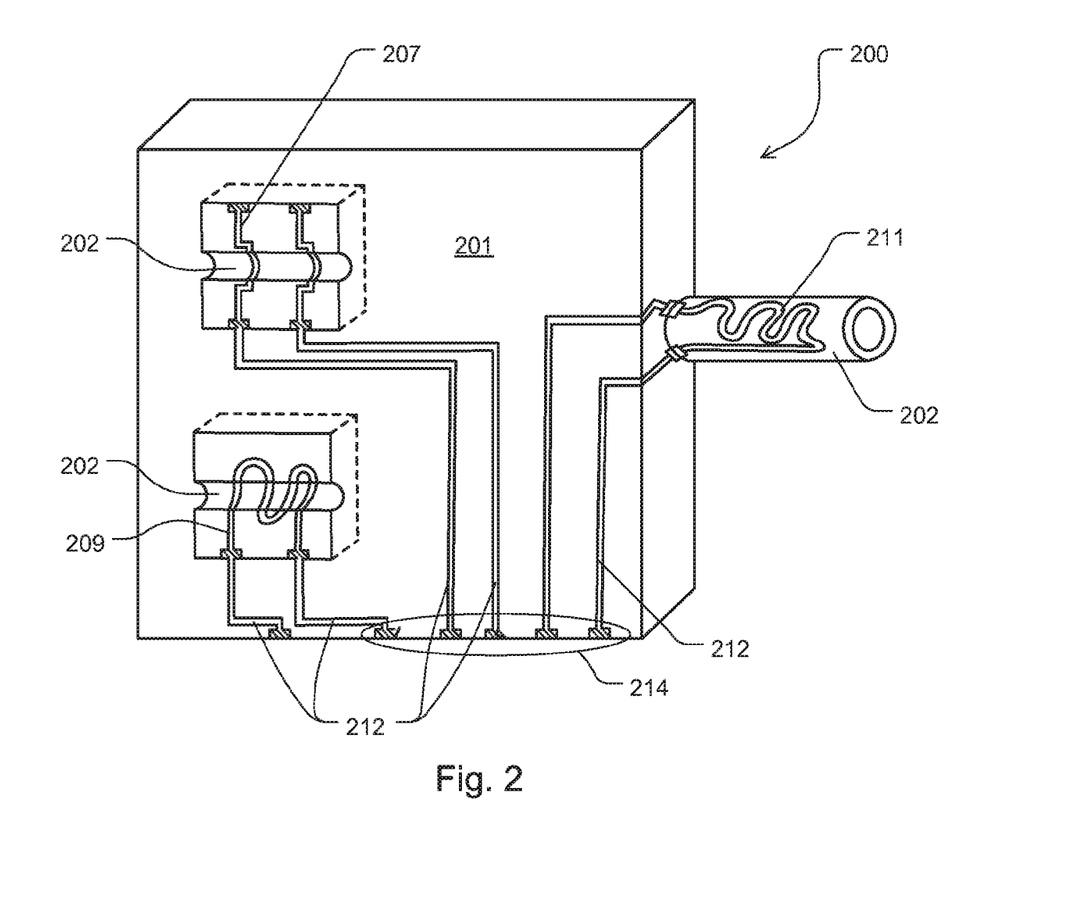
FIG. 2 shows a medical device 200 according to a second exemplary embodiment

FIG. 2 shows a medical device 200 according to a second exemplary embodiment.

The medical device 200 is presently again a partially functionalized disposable, with three different converters 207, 209, and 211.

A converter 207 for measuring the conductivity is exemplarily arranged in the upper left of FIG. 2. In the present simplified representation, the converter consists of two conductive paths which are applied by the additive, template-free printing method, in the interior of a fluid-conducting channel 202 of the device 200.

The two other converters 209, 211 show exemplary embodiments of pressure sensors. These can be arranged as strain gauges on the inner contour (see the converter 209) or on the outer contour (see the converter 211) of the fluid-conducting channel or tube 202 of the device 200.

Besides the converters 209, 211, FIG. 2 exemplarily shows the electromagnetic signal guide with conductive paths 212 towards the interface 300, here exemplarily a multipole connecting device 214. The conductive paths 212 towards the signal line may be applied onto the planar surface of the hard part 201 with the same additive and template-free method, in particular in the same production step.

However, non-planar (three-dimensional) line routings or runs, in the sense described supra, or crossings of (correspondingly insulated) lines are possible as well.

The conductive paths 212 may be applied by a second likewise additive and template-free printing method, for example, in a second production step, which follows the application of the converters 201, 209, 211. The entirety of the conductive paths 212 used to conduct signals from the location of the respective converter 207, 209, 211, which converts the parameter to be measured, e.g., into an electromagnetic signal, which itself is guided to the machine interface 300 by the conductive paths 212, can also contain individual parts which are applied by a two-component injection molding of conductive polymer.

Figure 3:
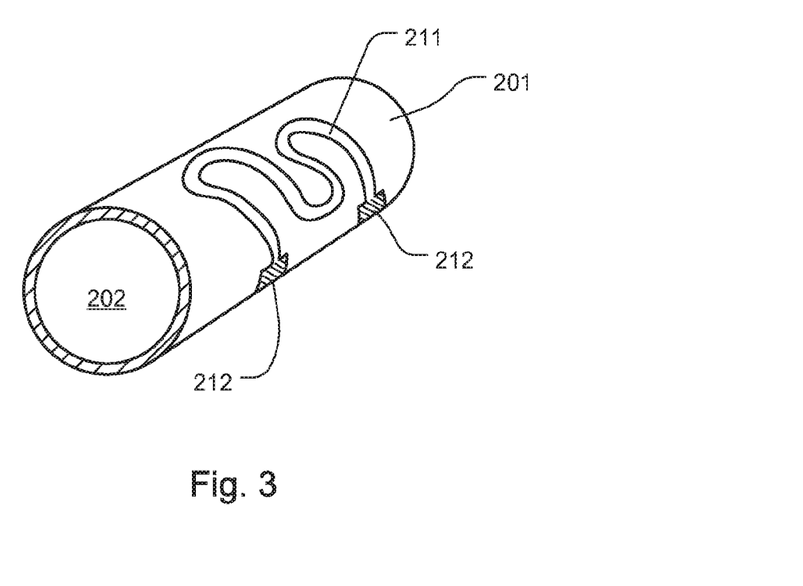
FIG. 3 shows a pressure converter discussed in FIG. 2 in an enlarged perspective.
Figure 4:
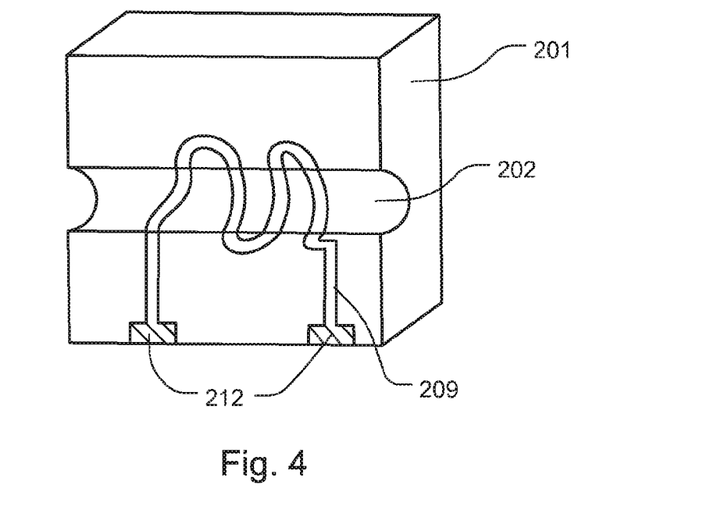
FIG. 4 shows a further pressure converter discussed in FIG. 2 in an enlarged perspective.

FIG. 3 and FIG. 4 show the pressure converters 209, 211 discussed in FIG. 2 in an enlarged perspective. They are only exemplarily designed as strain gauges. It can be seen that the converters 207, 209, 211 are applied by the additive and template-free printing method according to the present disclosure not only on a planar surface, but can also be routed in the third dimension via any topological shape.

For example, the structures of the internally additively applied pressure converter 209 extend over the edge of the surface of the illustrated half of the device 200 and then along the concave cavity of the fluid channel 202 as well as on the opposite side again over the edge at the surface.

The externally applied pressure converter 211 follows the cylindrical surface topology of the fluid-conducting channel or tube 202. This possibility of coating not only planar upper surfaces, but also any three-dimensional topologies with electrodes, conductive paths, etc. provides a further advantage for techniques used in the additive and template-free printing method according to the present disclosure.

The multi-connector 214, which serves, at the interface 300 to the machine side, for all the signals transmitted by the converter 207, 209, 211 from the device side may also be applied by an additive, template-free printing technique according to the present disclosure.

Figure 5:
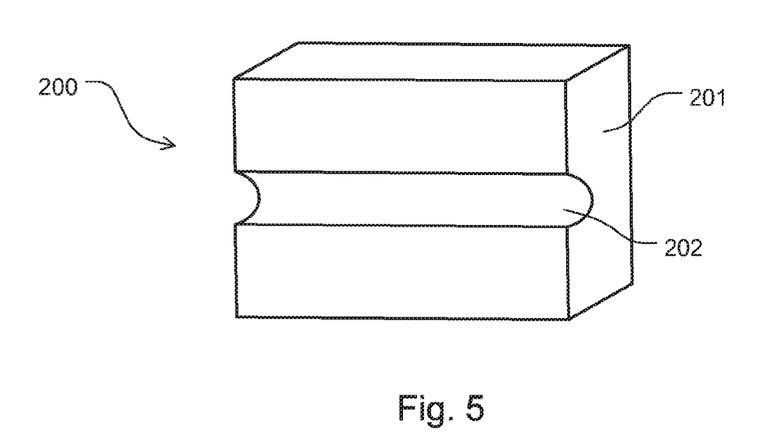
FIG. 5 shows a starting product of the production process for producing a medical device.

FIG. 5 shows a starting product of the production process according to the present disclosure for producing a partially functionalized disposable according to the present disclosure.

It may hereby be a hard part 201, which has been produced by injection molding. Moreover, FIG. 5 shows a fluid path 202 formed partially by the hard part 201.

The hard part 201 does not yet comprise a converter. The latter is applied in a subsequent application method. The result of this application is shown in FIG. 6.

Figure 6:
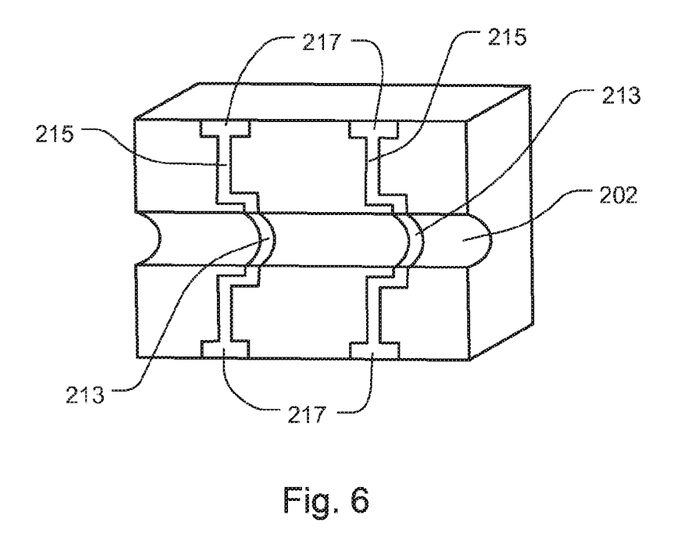
FIG. 6 shows the starting product of FIG. 5 after the application of converters.

FIG. 6 shows the hard part 201 of FIG. 5 after the additive application of a converter 213 with two conductive paths 215 and contacts 217, partly through the concave contour of the fluid path 202.

Further steps of the production method according to the present disclosure, not shown here, may include further post-processing steps on the electrodes, such as grinding, polishing, insulating, applying further functional layers of other materials, etc.

Finally, the printing of the signal connection to the machine interface as well as the printing of the multi-connector may take place. Both the conductive path and the multi-connecting device may be applied planar or three-dimensionally using one or more of the additive and template-free printing techniques according to the present disclosure. Here also, one or more post-processing steps are conceivable as described previously for the electrodes.

Further, two or more disposable parts prepared in this way may be combined, whereby also only individual parts thereof may contain components of the (partial) functionalization according to the present disclosure. For example, two disposable halves combined in the area of the fluid path may result in a closed channel with a circular cross-section. Furthermore, other channel geometries and cross-sectional forms are also conceivable. The second disposable half may also be just a flat cover so that all necessary recesses are arranged on the first half.

The second half may also be a membrane. Instead of a second disposable half, a seal or insulation of the surface of the first half may also be applied by one or more additional layers. These layers may be printed. They may also be produced by another known method and then be applied. Alternatively, the insulation or the sealing may also be applied in a further injection molding step by extrusion coating of the printed hard part.

Figure 7A:
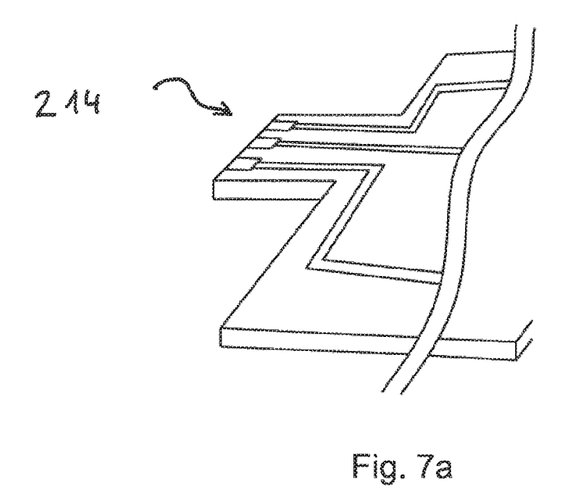
FIGS. 7a, 7b show a multi-connector or multipole connector.
Figure 7B:
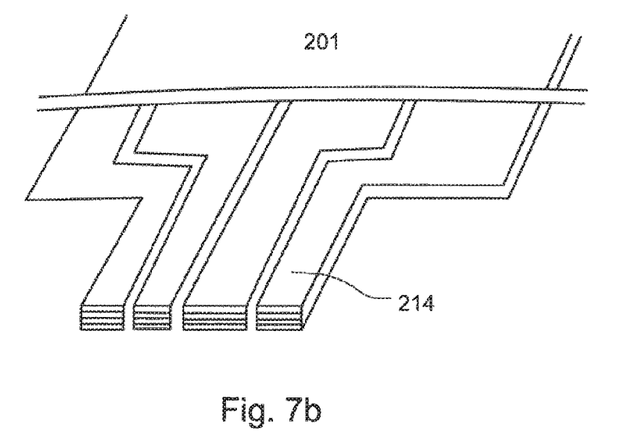

FIG. 7a shows as FIG. 7b the a.m. multipole connector 214 or multi-connecting device, which has been discussed in FIG. 2, in different views.

LIST OF REFERENCE NUMERALS 100 blood treatment apparatus
101 monitor
103 AD converter
200 blood cassette as an example of a medical device
201 cassette body or cassette main body, hard part, hard body, substrate
202 fluid path, channel, flow channel
203 conductive path or signal conductor
205 converter
207 converter
209 converter
211 DMS element as a conductor
212 conductive path or signal conductor
213 converter
214 multipole connecting device, multipole connector
215 conductive path
217 contact
300 interface, machine interface

The invention claimed is:

1. A device comprising:
  a hard part defining fluid paths for conducting a medical fluid through the hard part; and
  a converter arranged to measure a characteristic of the medical fluid while the medical fluid is present in one of the fluid paths,
  wherein the converter is applied or superimposed to the hard part by at least one additive application method comprising printing, and
  wherein the converter comprises:
    a converter to measure or determine pressure;
    a converter for capacitive measurements that includes two conductive surfaces and a dielectric placed between as a level determining converter or a distance determining converter;
    a converter having a dielectric placed between two conductive surfaces and that is operative for making capacitive measurements that indicate or determine a level or a distance;
    a converter that operates based on the piezoelectric effect;
    a magneto-inductive converter that operates as a flow measuring converter; or
    an optical converter.

2. The device according to claim 1, wherein the at least one additive application method comprises applying conducting ink.

3. The device according to claim 1, wherein the at least one application method comprises a template-free application.

4. The device according to claim 1, wherein the device comprises a plurality of converters, wherein a section of each of the converters is applied to the hard part by an additive application method.

5. The device according to claim 1, further comprising:
  a sensor arrangement comprising a plurality of sections applied to the device by the additive application method, wherein the sensor arrangement comprises the converter, or a plurality of sensor arrangements applied to the device by the additive application method.

6. The device according to claim 5, wherein at least one of the converter and the plurality of sections of the sensor arrangement are applied in the same production step.

7. The device according to claim 5, wherein the plurality of sections of the sensor arrangement comprise:
  at least one converter,
  at least one conductor, or
  at least one multipole connecting device.

8. The device according to claim 7, wherein the at least one converter is configured to measure or determine conductivity, pressure, tension, or current.

9. The device according to claim 7, wherein the application method includes a 2-dimensional or a 3-dimensional application method, and wherein at least one of the plurality of sections of the sensor arrangement and the at least one converter have been applied by the 2-dimensional or 3-dimensional application method.

10. The device 200 according to claim 7, wherein at least one of the plurality of sections and the at least one converter have been applied by injection molding.

11. The device according to claim 5, wherein at least a second additive application method is used for applying the plurality of sections of the sensor arrangement.

12. The device according to claim 1, wherein a multipole connecting device is applied to the device with the additive application method.

13. The device according to claim 1, wherein the medical device is a blood cassette.

14. The device according to claim 1, wherein the additive application method is a printing method.

15. The device according to claim 1, wherein the medical fluid is blood.

16. A method for producing a medical device, the method comprising:
  applying at least one converter to a hard part of the medical device by an additive application method comprising printing,
  wherein the at least one converter comprises:
    a converter to measure or determine pressure;
    a converter for capacitive measurements that includes two conductive surfaces and a dielectric placed between as a level determining converter or a distance determining converter;
    a converter having a dielectric placed between two conductive surfaces and that is operative for making capacitive measurements that indicate or determine a level or a distance;
    a converter that operates based on the piezoelectric effect;
    a magneto-inductive converter that operates as a flow measuring converter; or
    an optical converter.

17. The method according to claim 16, wherein the method further comprises:

(i) grinding, polishing, insulating, or applying further functional layers of other material on the at least one section;
(ii) printing a conductor on the device to provide a signal connection from the medical device to a machine;
(iii) printing a multipole connector on the medical device; and
(iv) combining at least two sections of the medical device which were applied by an additive application.

18. A treatment apparatus comprising:
a multipole connecter for connecting, or connected to the multipole connecting device of a medical device, and the medical device comprising:
  a hard part defining fluid paths for conducting a medical fluid through the hard part; and
  a converter arranged to measure a characteristic of the medical fluid while the medical fluid is present in one of the fluid paths,
  wherein the converter is applied or superimposed to the hard part by at least one additive application method comprising printing, and
  wherein the converter comprises:
    a converter to measure or determine pressure;
    a converter for capacitive measurements that includes two conductive surfaces and a dielectric placed between as a level determining converter or a distance determining converter;
    a converter having a dielectric placed between two conductive surfaces and that is operative for making capacitive measurements that indicate or determine a level or a distance;
    a converter that operates based on the piezoelectric effect;
    a magneto-inductive converter that operates as a flow measuring converter; or
    an optical converter.

19. The treatment apparatus according to claim 18, wherein the multipole connecting device is designed as an AD converter.

20. The treatment apparatus according to claim 18, wherein the treatment apparatus is a blood treatment apparatus, an apheresis device, dialysis device, a hemofiltration device, a hemodiafiltration device, a filtration device, or an apparatus for extracorporeal gas exchange.

* * * * *